US012176070B2

(12) United States Patent
Holt et al.

(10) Patent No.: US 12,176,070 B2
(45) Date of Patent: Dec. 24, 2024

(54) SYSTEMS AND METHODS FOR FACILITATING RAPID GENOME SEQUENCE ANALYSIS

(71) Applicant: UNIVERSITY OF UTAH RESEARCH FOUNDATION, Salt Lake City, UT (US)

(72) Inventors: Carson Hinton Holt, Lehi, UT (US); Mark Yandell, Salt Lake City, UT (US)

(73) Assignee: UNIVERSITY OF UTAH RESEARCH FOUNDATION, Salt Lake City, UT (US)

(*) Notice: Subject to any disclaimer, the term of this patent is extended or adjusted under 35 U.S.C. 154(b) by 83 days.

(21) Appl. No.: 17/724,115

(22) Filed: Apr. 19, 2022

(65) Prior Publication Data

US 2022/0336052 A1   Oct. 20, 2022

Related U.S. Application Data

(60) Provisional application No. 63/176,744, filed on Apr. 19, 2021.

(51) Int. Cl.
| | | |
|---|---|---|
| *G06F 17/30* | (2006.01) | |
| *G06F 16/176* | (2019.01) | |
| *G16B 30/10* | (2019.01) | |
| *G16B 50/50* | (2019.01) | |

(52) U.S. Cl.
CPC ........... *G16B 30/10* (2019.02); *G06F 16/176* (2019.01); *G16B 50/50* (2019.02)

(58) Field of Classification Search
CPC ........ G06F 16/13; G06F 16/24; G06F 16/156; G06F 19/22; C12Q 1/6869; G06N 3/00; G06N 5/00; G05B 13/00
See application file for complete search history.

(56) References Cited

U.S. PATENT DOCUMENTS

| | | | | |
|---|---|---|---|---|
| 5,935,793 A | * | 8/1999 | Wong ................... | C12Q 1/6869 435/6.12 |
| 6,480,791 B1 | * | 11/2002 | Strathmann .......... | C12Q 1/6876 506/3 |
| 6,534,293 B1 | * | 3/2003 | Barany ................ | C12Q 1/6827 536/23.1 |
| 6,828,100 B1 | * | 12/2004 | Ronaghi .............. | C12Q 1/6869 435/6.12 |
| 7,544,473 B2 | * | 6/2009 | Brenner ............... | C12Q 1/6827 435/6.12 |

(Continued)

*Primary Examiner* — Hung D Le
(74) *Attorney, Agent, or Firm* — Workman Nydegger

(57) ABSTRACT

A method for facilitating rapid genome sequence analysis includes accessing an output stream of an alignment process that includes aligned reads of a biological sequence that are aligned to a reference genome. The method also includes distributing the aligned reads to a plurality of computing nodes based on genomic position. Each of the plurality of computing nodes is assigned to a separate data bin of a plurality of data bins associated with genomic position. The method also includes, for at least one aligned read determined to overlap separate data bins of the plurality of data bins, duplicating the at least one aligned read and distributing the at least one aligned read to separate computing nodes of the plurality of computing nodes that are assigned to the separate data bins.

12 Claims, 11 Drawing Sheets

(56) References Cited

U.S. PATENT DOCUMENTS

| | | | | |
|---|---|---|---|---|
| 7,565,346 B2* | 7/2009 | Fan | ............... | G06F 18/22 |
| 8,765,382 B2* | 7/2014 | Drmanac | ............... | G01N 15/1404 |
| | | | | 435/6.12 |
| 9,328,382 B2* | 5/2016 | Drmanac | ............... | C12Q 1/6869 |
| 9,890,425 B2* | 2/2018 | Domanus | ............... | C12Q 1/686 |
| 10,233,490 B2* | 3/2019 | Stapleton | ............... | C12Q 1/6869 |
| 11,488,688 B2* | 11/2022 | Kural | ............... | G16B 30/20 |
| 11,859,171 B2* | 1/2024 | Quake | ............... | C12N 15/1065 |
| 2002/0197621 A1* | 12/2002 | Drmanac | ............... | C12Q 1/6874 |
| | | | | 435/6.12 |
| 2003/0044784 A1* | 3/2003 | Jones | ............... | C12Q 1/6844 |
| | | | | 435/6.1 |
| 2003/0092007 A1* | 5/2003 | Gibbs | ............... | C12N 15/1034 |
| | | | | 506/14 |
| 2003/0148313 A1* | 8/2003 | Strathmann | ............... | C12Q 1/6837 |
| | | | | 506/10 |
| 2004/0029165 A1* | 2/2004 | Wong | ............... | C12Q 1/6874 |
| | | | | 435/6.12 |
| 2004/0059721 A1* | 3/2004 | Patzer | ............... | G16B 50/00 |
| 2004/0248161 A1* | 12/2004 | Rothberg | ............... | C12Q 1/6827 |
| | | | | 435/6.1 |
| 2005/0042633 A1* | 2/2005 | Williams | ............... | C12Q 1/6869 |
| | | | | 435/6.12 |
| 2005/0130173 A1* | 6/2005 | Leamon | ............... | G01N 21/253 |
| | | | | 435/5 |
| 2006/0024681 A1* | 2/2006 | Smith | ............... | C12Q 1/6806 |
| | | | | 435/6.1 |
| 2008/0318796 A1* | 12/2008 | Drmanac | ............... | C12Q 1/686 |
| | | | | 506/3 |
| 2009/0005252 A1* | 1/2009 | Drmanac | ............... | C12Q 1/6874 |
| | | | | 506/3 |
| 2009/0011943 A1* | 1/2009 | Drmanac | ............... | C12N 15/66 |
| | | | | 506/4 |
| 2009/0099041 A1* | 4/2009 | Church | ............... | C12Q 1/6837 |
| | | | | 506/26 |
| 2009/0307218 A1* | 12/2009 | Selly | ............... | G16B 30/00 |
| 2010/0199155 A1* | 8/2010 | Kermani | ............... | H03M 13/1515 |
| | | | | 714/752 |
| 2011/0008775 A1* | 1/2011 | Gao | ............... | C12Q 1/6869 |
| | | | | 435/6.1 |
| 2011/0033854 A1* | 2/2011 | Drmanac | ............... | B01J 19/0046 |
| | | | | 435/6.12 |
| 2013/0059740 A1* | 3/2013 | Drmanac | ............... | G16B 30/00 |
| | | | | 506/4 |
| 2013/0124100 A1* | 5/2013 | Drmanac | ............... | G16B 30/10 |
| | | | | 702/20 |
| 2014/0228223 A1* | 8/2014 | Gnirke | ............... | C12N 15/1031 |
| | | | | 506/14 |
| 2014/0274731 A1* | 9/2014 | Raymond | ............... | C12Q 1/6806 |
| | | | | 506/17 |
| 2015/0044687 A1* | 2/2015 | Schmitt | ............... | C12Q 1/6876 |
| | | | | 435/6.12 |
| 2015/0344873 A1* | 12/2015 | Xiao | ............... | C12Q 1/6806 |
| | | | | 506/26 |
| 2018/0300451 A1* | 10/2018 | Burke | ............... | G16B 40/20 |
| 2019/0080045 A1* | 3/2019 | Wei | ............... | G16B 15/00 |
| 2021/0047683 A1* | 2/2021 | Chen | ............... | C12Q 1/6834 |
| 2022/0298545 A1* | 9/2022 | Chen | ............... | C12Q 1/6806 |
| 2023/0030373 A1* | 2/2023 | Vaughan | ............... | G16B 30/00 |

* cited by examiner

900

902
Accessing A Plurality Of Files, Each Of The Plurality Of Files Being Stored Locally On A Separate Computing Node Of A Plurality Of Computing Nodes, Each Of The Plurality Of Files Being Generated Based On Aligned Reads Of A Biological Sequence That Are Aligned To A Reference Genome, Each Particular File Of The Plurality Of Files Comprising Non-Indexed Independent Compression Blocks, Each File Of The Plurality Of Files Comprising One Or More Compressed Representations Of One Or More Redundant Data Entries At A Start Of The File Or At An End Of The File, The One Or More Redundant Data Entries Being Represented In At Least One Separate File Of The Plurality Of Files

904
For Each Particular File Of The Plurality Of Files, Determining A Respective Region Of Interest By Selectively Decompressing Fewer Than All Of The Independent Compression Blocks Of The Particular File To Identify A Respective Start Boundary Or A Respective End Boundary For The Particular File, The Respective Region Of Interest Being Bounded By At Least The Respective Start Boundary Or The Respective End Boundary, Wherein Data Entries Preceding The Respective Start Boundary Are Represented In At Least One Separate File Of The Plurality Of Files, And Wherein Data Entries Following The Respective End Boundary Are Represented In At Least One Separate File Of The Plurality Of Files

906
Generating A Merged File From The Plurality Of Files By Causing Each Particular Computing Node Of The Plurality Of Computing Nodes To Write Respective Data Entries From Compression Blocks Within The Respective Region Of Interest Of The Corresponding File To Generate The Merged File In Parallel

FIG. 9

SYSTEMS AND METHODS FOR FACILITATING RAPID GENOME SEQUENCE ANALYSIS

CROSS-REFERENCE TO RELATED APPLICATIONS

This application claims priority to and the benefit of U.S. Provisional Patent Application Ser. No. 63/176,744, filed Apr. 19, 2021 and titled "Systems and Methods for Facilitating Rapid Genome Sequence Analysis," the entirety of which is incorporated herein by this reference.

BACKGROUND

Next generation sequencing (NGS), also known as high-throughput sequencing, has revolutionized genetic analysis by allowing for the rapid analysis of large amounts of genetic information. NGS encompasses several sequencing technologies that provide a significant improvement over earlier technologies such as Sanger sequencing. NGS allows for whole genome or exome sequencing to be completed faster and with less expense, with high accuracy. NGS relies on technologies that have the ability to sequence many short overlapping sequences of amplified genetic material.

Advances in NGS have enabled large-scale projects that are focused on the sequencing of complete genomes for large numbers of individuals. NGS is actively used in a variety of disciplines such as oncology, where NGS is used to routinely screen for mutations in melanoma, breast cancer, and lung cancer patients. Additionally, multiple oncogenes have been identified through research with NGS.

Wet lab processing and sequencing of material is only the first step in the overall NGS process. Computer methods and analytic software are needed to understand the wealth of information generated by NGS. These computational tools include program suites such as Burrows-Wheeler Aligner (BWA), Bowtie, Galaxy, SanGeniX, and/or others. These tools assist in the multitude of steps needed to analyze the sequenced material, such as quality assessment, alignment of sequences, variant identification and annotation, visualization, etcetera.

Currently, there are a variety of tools used to facilitate variant identification and annotation. Commonly used proprietary software for variant identification and annotation are SanGeniX1 and DNAStar2.

Due to the large amount of data involved in whole genome analysis, significant computer power and time, often on the order of days, are needed for alignment and analysis. Accordingly, there is an ongoing need and desire for improved systems and methods for facilitating rapid genome sequence analysis.

The subject matter claimed herein is not limited to embodiments that solve any disadvantages or that operate only in environments such as those described above. Rather, this background is only provided to illustrate one exemplary technology area where some embodiments described herein may be practiced.

SUMMARY

Implementations of the present disclosure extend at least to systems and methods for facilitating rapid genome sequence analysis.

Some embodiments provide a method that includes accessing an output stream of an alignment process that includes aligned reads of a biological sequence that are aligned to a reference genome. The method also includes distributing the aligned reads to a plurality of computing nodes based on genomic position. Each of the plurality of computing nodes is assigned to a separate data bin of a plurality of data bins associated with genomic position. The method also includes, for at least one aligned read determined to overlap separate data bins of the plurality of data bins, duplicating the at least one aligned read and distributing the at least one aligned read to separate computing nodes of the plurality of computing nodes that are assigned to the separate data bins.

Some embodiments provide a method that includes accessing a plurality of files. Each of the plurality of files is stored locally on a separate computing node of a plurality of computing nodes. Each of the plurality of files is generated based on aligned reads of a biological sequence that are aligned to a reference genome. Furthermore, each particular file of the plurality of files includes non-indexed independent compression blocks. Also, each file of the plurality of files includes one or more compressed representations of one or more redundant data entries at a start of the file or at an end of the file. The one or more redundant data entries is represented in at least one separate file of the plurality of files.

The method also includes, for each particular file of the plurality of files, determining a respective region of interest by selectively decompressing fewer than all of the independent compression blocks of the particular file to identify a respective start boundary or a respective end boundary for the particular file. The respective region of interest is bounded by at least the respective start boundary or the respective end boundary. Data entries preceding the respective start boundary are represented in at least one separate file of the plurality of files, and data entries following the respective end boundary are represented in at least one separate file of the plurality of files.

The method also includes generating a merged file from the plurality of files by causing each particular computing node of the plurality of computing nodes to write respective data entries from compression blocks within the respective region of interest of the corresponding file to generate the merged file in parallel.

Some embodiments provide a method that includes accessing a merged file. The merged file includes a plurality of aligned reads of a biological sequence. The plurality of aligned reads is written to the merged file from respective files of a plurality of computing nodes. The respective files are generated based on binning alignment output that aligns initial reads of an initial biological sequence file to a reference genome. The merged file also includes analysis data for each of the plurality of aligned reads. The analysis data are written to the merged file from the respective files of the plurality of computing nodes. The analysis data are generated at the plurality of computing nodes for the respective files.

The method also includes generating a first plurality of hashes comprising a hash for each of the plurality of aligned reads of the merged file, and generating a second plurality of hashes comprising a hash for each initial read of the initial biological sequence file. The method also includes validating the merged file by performing a comparison between the first plurality of hashes and the second plurality of hashes.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description which follows, and in part will be obvious from the description, or may be learned by the practice of the teachings herein. Features and advantages of the invention may be realized and obtained by means of the instruments and combinations particularly pointed out in the appended claims. Features of the present invention will become more fully apparent from the following description and appended claims or may be learned by the practice of the invention as set forth hereinafter.

BRIEF DESCRIPTION OF THE DRAWINGS

In order to describe the manner in which the above-recited and other advantages and features can be obtained, a more particular description of the subject matter briefly described above will be rendered by reference to specific embodiments which are illustrated in the appended drawings. Understanding that these drawings depict only typical embodiments and are not therefore to be considered to be limiting in scope, embodiments will be described and explained with additional specificity and detail through the use of the accompanying drawings.

FIGS. 8-10 illustrate example flow diagrams depicting acts associated with facilitating rapid genome sequence analysis.

DETAILED DESCRIPTION

Implementations of the present disclosure extend at least to systems and methods for facilitating rapid genome sequence analysis. Attention will now be directed to FIGS. 1 through 11, which provide various supporting illustrations related to the disclosed embodiments.

Parallel Alignment Processes & Distribution to Data Bins

Figure 1A:
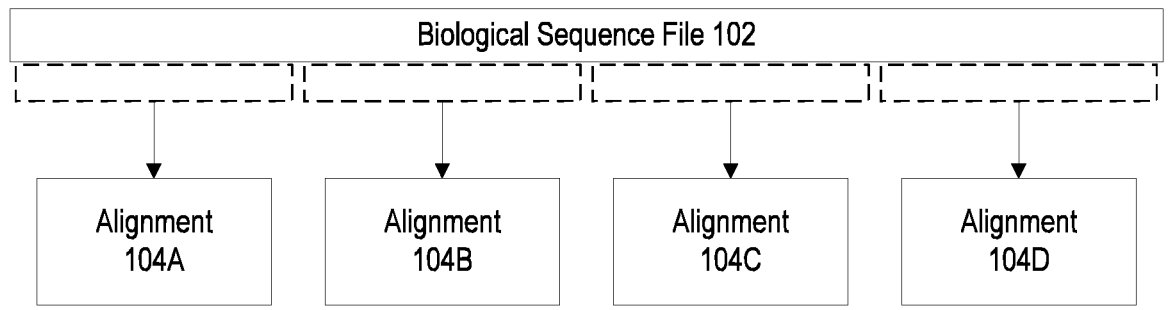
FIGS. 1A and 1B illustrate a conceptual representation of performing parallel alignment processes on a biological sequence file and distributing the output from the alignment processes to data bins.
Figure 1B:
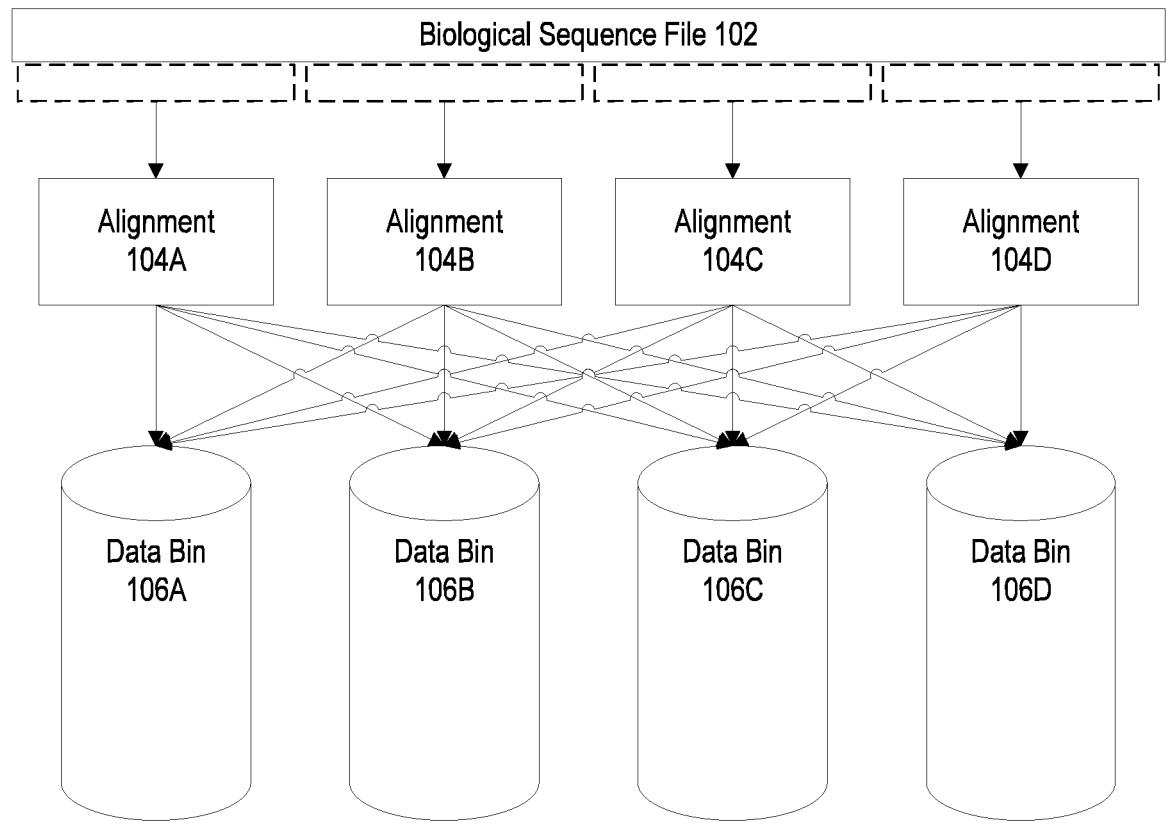

FIGS. 1A and 1B illustrate a conceptual representation of performing parallel alignment processes on a biological sequence file and distributing the output from the alignment processes to data bins. In particular, FIG. 1A shows a biological sequence file 102, which may store data resulting from the performance of one or more biological sequencing processes. The biological sequence file 102 may take on various formats such as the FASTQ format, which stores sequence reads together with base quality information/scores. Compressed FASTQ files for a single genome can include a file size of about 50-100 GB or greater.

Many types of insights can be revealed by comparing a biological sequence with a reference genome, such as burden analysis (e.g., VAAST analysis for identifying genes enriched for coding genetic changes in a population of interest), SNP and haplotype statistical analysis (e.g., using GPAT), identifying gene lists of causal candidates of interest (e.g., for genetic disease treatment and/or for in vivo experimentation to reveal the underlying causes of phenotypes of interest), and/or others.

As indicated above, preparing raw sequencing data (e.g., biological sequence file 102) for such downstream analysis is computationally intensive, and can prove overwhelming and/or prohibitive for studies that involve sequencing data for multiple subjects or individuals.

Accordingly, implementations of the present disclosure are directed to processing techniques for facilitating rapid analysis of biological sequences. Techniques disclosed herein are typically performed using one or more compute clusters that include a plurality of interconnected computing nodes capable of coordinating/communicating with one another (e.g., via message passing interface or MPI) to carry out processing tasks. Each computing node may include any number of processors (e.g., one or more CPUs, one or more of which may act as a gatekeeper for managing other CPUs) which each may run any number of threads to facilitate the functions described herein (e.g., a communication thread, a worker thread, an input/output thread, etc.). Additional details regarding compute clusters and computing nodes will be provided hereinafter.

Various computing nodes of a compute cluster may perform alignment processes on the sequence reads represented in the biological sequence file 102 to align the reads to a reference genome. For example, FIG. 1A depicts the biological sequence file 102 divided into sections marked by dashed boxes underneath the biological sequence file 102. These boxes represent different file offsets for streaming chunks of data from the biological sequence file 102 to multiple computing nodes. FIG. 1A illustrates alignment processes 104A-104D, which may be performed in parallel using separate computing nodes of one or more compute clusters (thereby increasing compute speed associated with aligning reads of the biological sequence file 102 to a reference genome).

The alignment processes 104A-104D depicted in FIG. 1A may comprise any suitable alignment process, such as a Burrows-Wheeler Aligner (BWA). Although FIG. 1A (and other Figures described herein) focuses, in at least some respects, on implementations that utilize four computing nodes of a compute cluster, one will appreciate, in view of the present disclosure, that techniques described herein may utilize any number of computing nodes, such as more or fewer than four computing nodes.

The output of the various alignment processes 104A-104D may be regarded as an output stream that includes aligned reads from the biological sequence file 102 that are aligned to a reference genome. To facilitate rapid analysis of the genome sequence represented in the biological sequence file 102 (e.g., relative to the reference genome), the aligned reads represented in the output stream of the alignment processes 104A-104D may be assigned to various data bins 106A-106D (depicted in FIG. 1B by the various lines extending from the alignment processes 104A-104D to the various data bins 106A-106D).

In some instances, each data bin 106A-106D is associated with a computing node (e.g., separate computing nodes, in some instances), such that assigning an aligned read to a data bin 106A-106D corresponds to distributing the aligned read to a computing node. For example, the aligned reads may be buffered and sent as MPI messages to one or more computing nodes each time the buffer fills. In this way, aligned reads assigned to data bins 106A-106D may be passed to designated computing nodes as the bins grow, which, as will be described in more detail hereinafter, may allow processing on the aligned reads to begin/proceed at the designated computing nodes while the alignment processes 104A-104D are still running.

In some instances, bin sizes of the data bins 106A-106D are limited to powers of two (e.g., 2^20 providing a bin size of 1,048,576). Limiting bin sizes to powers of two may facilitate computationally inexpensive bin determination for aligned reads. For example, when bin sizes are limited to powers of two, a computationally efficient bit shift operation may be performed on one or more genomic positions associated with the aligned read (e.g., reference positions/locations of pairs or mates of an aligned read) to determine an appropriate bin for the aligned read. In this regard, different data bins 106A-106D may be associated with particular genomic positions and thereby configured to receive aligned reads that include mates/pairs of particular genomic positions.

In some instances, one or more aligned reads from the output stream of the alignment processes 104A-104D are assigned to multiple data bins 106A-106D. For example, a particular aligned read may be determined to overlap a genomic position boundary between two data bins, such as where bit shifting operations performed on different genomic positions associated with the particular aligned read result in different data bin assignments. In such instances, the particular aligned read may be duplicated and distributed to both data bins.

Assigning aligned reads that border bin boundaries to multiple data bins 104A-104D results in data redundancy in files based on the aligned reads generated at the various computing nodes associated with the various data bins 106A-106D. In this regard, a data bin can receive read data that overlaps with read data of an adjacent data bin (e.g., with an overlap of up to 30 kb, in some instances). As will be described in more detail hereinafter, such data redundancy can advantageously allow for regional analyses to be performed on such files simultaneously at separate computing nodes and/or can facilitate recombination of the files to form a merged file using a no-index approach.

Local File Generation

Figure 2:
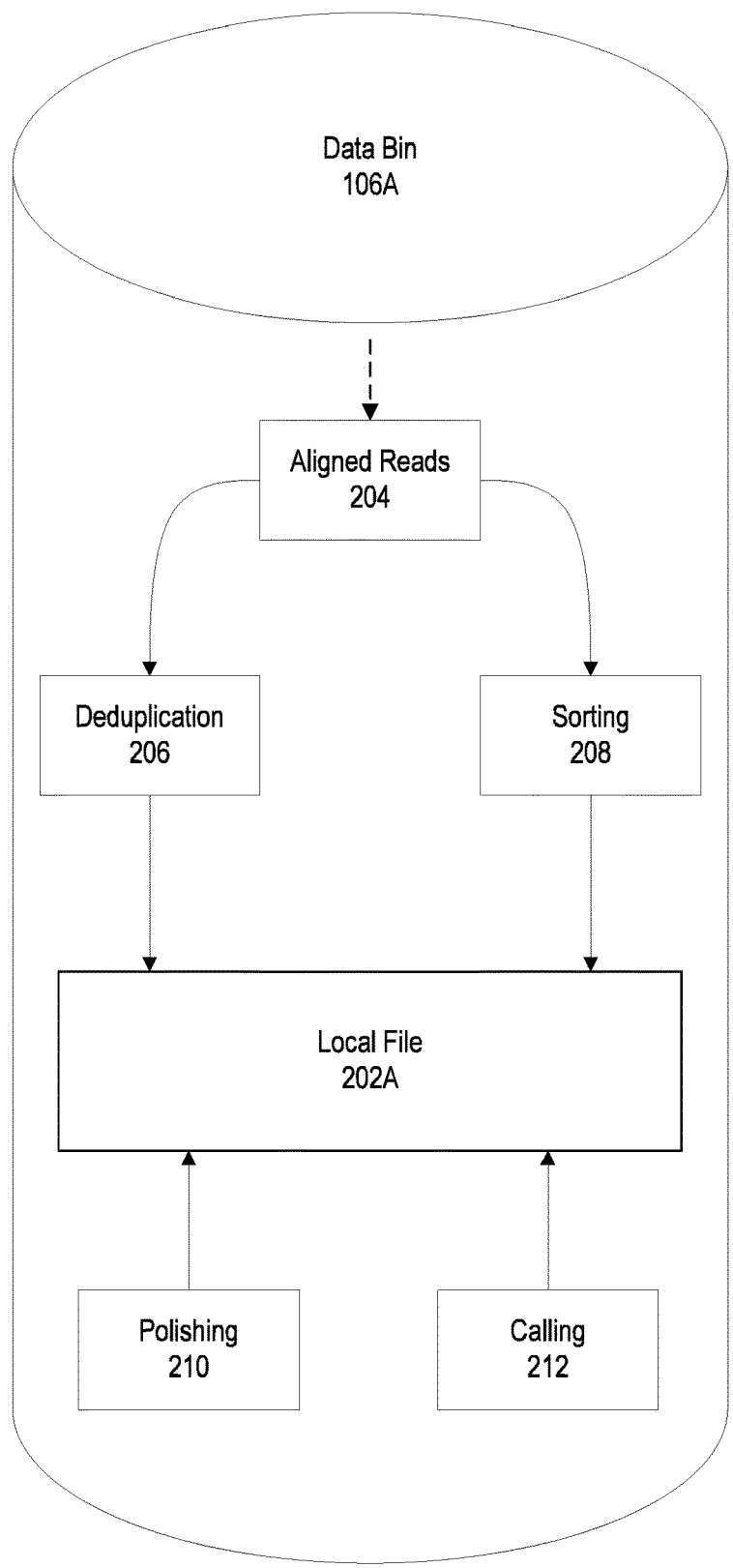
FIG. 2 illustrates a conceptual representation of generating a local file at a computing node associated with a data bin based on aligned reads.

FIG. 2 illustrates a conceptual representation of generating a local file 202A at a computing node associated with data bin 106A based on aligned reads 204. The aligned reads 204 depicted in FIG. 2 may at least partially correspond to aligned reads output from the alignment processes 104A-104D and assigned to data bin 106A. One will appreciate, in view of the present disclosure, that the operations and/or techniques discussed with reference to FIG. 2 may be applied by other computing nodes associated with other data bins (e.g., data bins 106B-106D, and/or others).

As depicted in FIG. 2, as aligned reads 204 received by the computing node associated with data bin 106A are streamed to deduplication processes 206 and/or sorting processes 208. The aligned reads 204 may be streamed to such processes as the data bin 106A grows and without waiting for all aligned reads to be distributed or assigned to the data bin 106A. In this way, deduplication processes 206 and/or sorting processes 208 may advantageously be performed at least partially contemporaneously with one another and/or with the distribution of aligned reads to the computing nodes associated with the various data bins 106A-106D (e.g., depicted in FIG. 1B as output from the alignment processes 104A-104D directed toward the various data bins 106A-106D).

The deduplication process(es) 206 may comprise a Samblaster deduplication operation and/or other suitable deduplication operation. The sorting process(es) 208 may comprise a Sambamba sort operation and/or other suitable sort operation. Performing the deduplication processes 206 and/or sorting processes 208 on the computing node associated with data bin 106A allows the computing node to locally store a file 202A of aligned reads 204 that are deduplicated and/or sorted. This local file 202A can serve as a safe substrate for performing secondary analysis at the regional level (i.e., on a subset of the aligned reads derived from the biological sequence file 102, rather than all reads in linear fashion). Other local files 202B-202D (see FIG. 4) can be generated at other computing nodes associated with other data bins 106B-106D, such that secondary analysis can advantageously be performed in parallel on different aligned reads derived from the biological sequence file 102. Such secondary analysis may advantageously be performed prior to merging the different files to form a composite or merged resulting file (merging will be described hereinafter).

The local file 202A may be stored in various formats, such as the BAM format, the BGZF format, and/or others. Secondary analysis performed using the local file 202A may include polishing processes 210, variant calling processes 212, and/or others. Polishing process(es) 210 may comprise GATK IndelRealigner and/or BaseRecalibrator operation(s), Pilon, Racon, and/or other operations to update the local file 202A. Calling process(es) 212 may utilize a HaplotypeCaller, which may generate a regional VCF or gVCF file. Although only a single local file 202A is depicted in FIG. 2, one will appreciate, in view of the present disclosure, that any number of local files can be generated at the computing node associated with data bin 106A (and/or any other data bin). For example, a regional BAM file, regional BGZF file, regional VCF file, and/or regional gVCF file may be generated at the computing node in association with the aligned reads 204 assigned to the data bin 106A.

Redundant Data Entries & Generation of Merged File

Figure 3A:
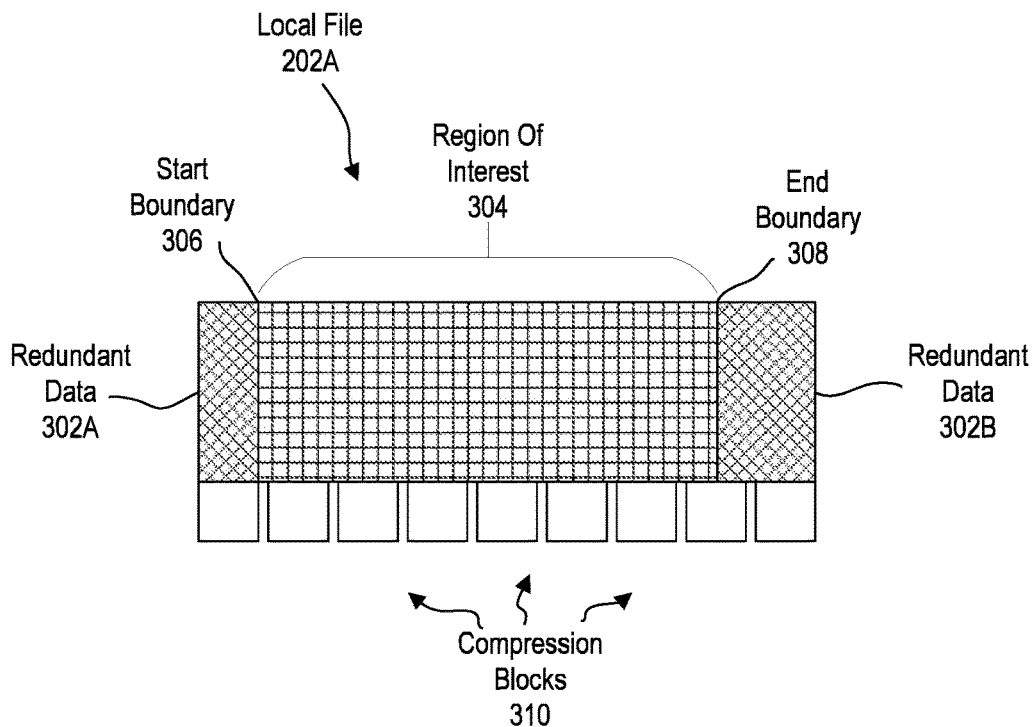
FIGS. 3A and 3B illustrate a conceptual representation of a local file including redundant data entries.
Figure 3B:
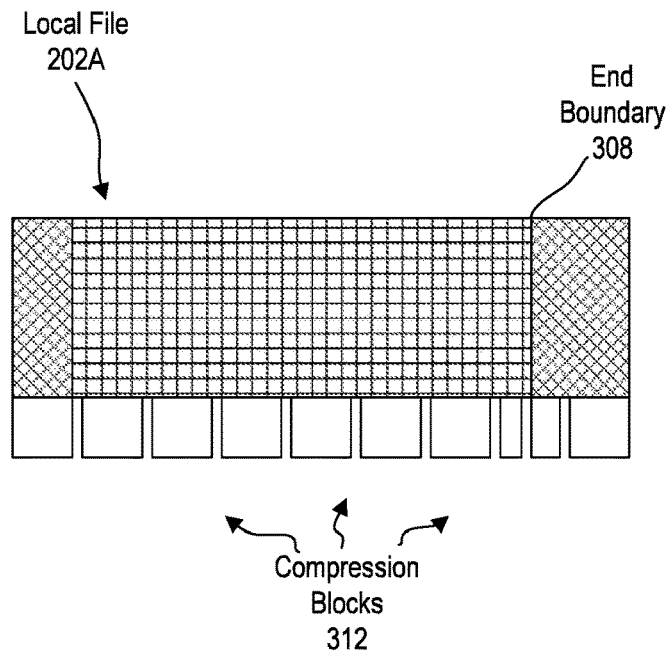

FIGS. 3A and 3B illustrate conceptual representations of the local file 202A from FIG. 2. As indicated above, aligned reads can become duplicated and distributed to multiple data bins (e.g., where an aligned read includes different elements at different genomic positions that are associated with different adjacent data bins). Thus, as shown in FIG. 3A, the local file 202A can include redundant data 302A at a start of the local file 202A and redundant data 302B at and end of the file 202A. The redundant data 302A and 302B may include representations of aligned reads (and/or variant data) that were also distributed to other data bins (e.g., data bins neighboring data bin 106A). Thus, the redundant data 302A and 302B may include data entries that are represented in at least one separate file (e.g., local file 202B, see FIG. 4) locally stored at a separate computing node (e.g., a computing node associated with data bin 106B).

Although FIG. 3A depicts redundant data 302A and 302B data at both the start and the end of the local file 202A, one will appreciate, in view of the present disclosure, that a local file may, in some instances, include redundant data at only the start or only the end thereof.

Separate from the redundant data 302A and 302B, the local file 202A shown in FIG. 3A includes a region of interest 304 that includes data entries that are based on aligned reads that were only assigned to the data bin 106A (and/or to the computing node associated with data bin 106A). In this regard, data entries within the region of interest may be regarded as unique to the data bin 106A relative to the other data bins 106B-106D (and/or unique to the computing node associated with data bin 106A relative to the other computing nodes associated with the other data bins 106B-106D).

FIG. 3A shows a start boundary 306 and an end boundary 308 demarcating the boundaries between the region of interest 304 and the redundant data 302A and 302B. When merging the local file 202A with other local files of other computing nodes to generate a merged file, care must be exercised to prevent duplicative writing of data entries that are included outside of the regions of interest of the various local files (e.g., local files 202A-202D, see FIG. 4). However, as noted above, the local file 202A may be stored in a compressed format, such as the BAM format, the BGZF format, or another format. Accordingly, FIG. 3A depicts compression blocks 310 of the local file 202A, which may independently store portions of the data represented in the local file 202A in a compressed manner.

Although utilizing independent compression blocks 310 to store the data entries (based on the aligned reads) of the local file 202A can provide various advantages, the use the independent compression blocks 310 can render the start boundary 306 and/or the end boundary 308 surrounding the region of interest 304 unclear, absent performing computationally costly decompression operations and/or indexing operations to locate the boundaries. For example, FIG. 3A shows the end boundary 308 being internal to a compression block 310 toward the end of the local file 202A.

In accordance with the present disclosure, because the redundant data 302A and 302B is predictably located at the beginning and/or the end of the local file 202A (in view of the techniques for binning the aligned reads as described hereinabove), the start boundary 306 and/or the end boundary 308 may be located without indexing and without performing decompression operations on all compression blocks 310 of the local file 202A. Decompression operations may be performed in a guided, semi-random, or random fashion on fewer than all of the compression blocks 310 to locate the start boundary 306 and/or the end boundary 308. For example, decompression operations may be performed toward the end of a first local file and toward the beginning of a neighboring second local file (e.g., a local file associated with a neighboring data bin). The data identified from the neighboring first and second local files may be compared to identify duplicative data and to determine the end boundary of the first local file and the start boundary of the second local file.

Figure 4:
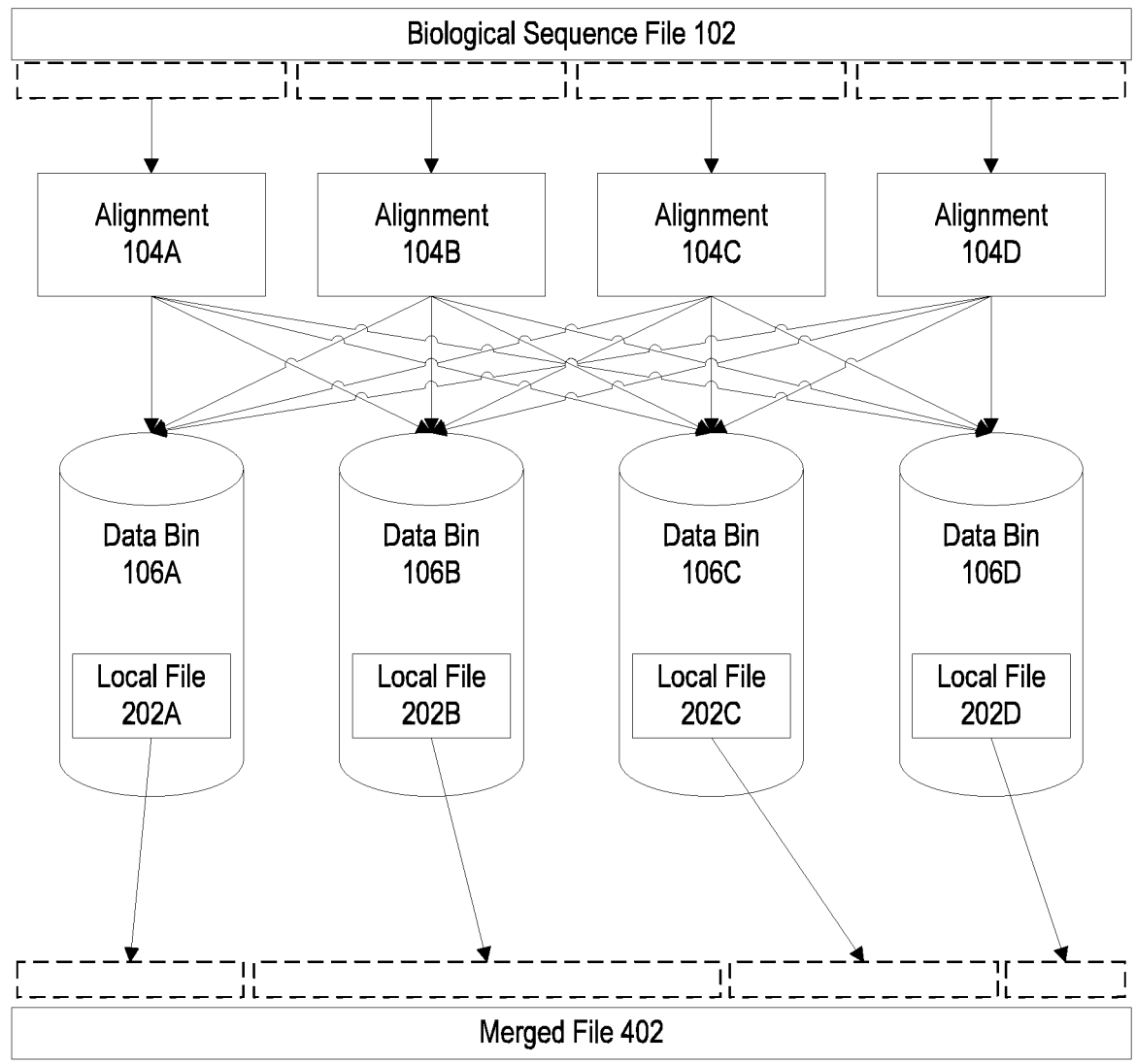
FIG. 4 illustrates a conceptual representation of generating a merged file using local files associated with various data bins.

By identifying start boundaries and/or end boundaries of local files that include independent non-indexed compression blocks, care can be exercised when merging the local files to prevent duplication of data entries in the merged file (see FIG. 4).

In some instances, as shown in FIG. 3A, a start boundary 306 and/or an end boundary 308 of a local file 202A may reside within a compression block 310. In some instances, to simplify write operations for forming a merged file, compression blocks 310 may be split and recombined to cause a start boundary and/or end boundary to coincide with a transition between adjacent compression blocks (e.g., causing a start boundary to coincide with an end of a compression block, or causing an end boundary to coincide with a start of a compression block). For example, FIG. 3B shows modified compression blocks 312 where a compression block 310 that originally stored the end boundary 308 at a middle portion thereof has been split and recombined/rebuilt into separate compression blocks to allow the end boundary 308 to exist at a transition between compression blocks (e.g., at a start of a compression block).

In this way, when writing from the local file 202A in combination with other local files to generate a merged file, systems may simply ignore entire compression blocks to avoid writing duplicative data entries. FIG. 4 illustrates elements shown and described with reference to FIGS. 1A and 1B, as well as local files 202A-202D locally stored at computing nodes associated with the different data bins 106A-106D. FIG. 4 illustrates the computing nodes performing write operations from their respective local files 202A-202D to generate a merged file 402 at a common shared location. A merged file 402 may comprise a BAM, BGZF, VCF, gVCF, or another file format.

The various computing nodes may write from the respective regions of interest for the local files 202A-202D, and coordination among the computing nodes may be facilitated to ensure that only one copy of data represented in multiple local files becomes written to the merged file 402. For example, a computing node may write data from a region of interest of its local file(s) while refraining from writing data from one or more redundant data sections at the start or end of the local file(s). The write operations of the various computing nodes may be performed in parallel to allow for rapid generation of the merged file 402. In some instances, a file system optimized for parallel write operations (e.g., Lustre) is used to allow for write speeds on the order of hundreds of gigabytes per second.

Furthermore, as noted above, local files 202A-202D can include various types of data (e.g., in any number of respective files), such as alignment data and/or variant data. In this way, a merged file 402 may be generated as a combined BAM or BGZF file (e.g., from regional BAM or BGZF files of the different data bins 106A-106D) and/or a combined VCF or gVCF file (e.g., from regional VCF or gVCF files of the different data bins 106A-106D). In addition, merging of alignment data to form a merged BAM or BGZF file is independent of variant calling on the regional local files 202A-202D, so the calling process(es) 212 discussed above with reference to FIG. 2 may be performed independent of and/or in parallel with the writing of a merged BAM or BGZF file, and the writing of a merged VCF or gVCF file may be performed independent of and/or in parallel with the writing of a merged BAM or BGZF file.

In some instances, to generate a merged file 402, a new file is pre-allocated based on an expected size of the merged file 402. The expected size of the merged file 402 can be determined based on the size of the local files 202A-202D that will be combined to form the merged file 402 (e.g., based on the sizes of the regions of interest and/or redundant data sections of the local files 202A-202D). Furthermore, based on the sizes of the local files 202A-202D, a write operation offset may be determined for each computing node that will perform write operations to form the merged file 402. For each particular computing node, a write operation offset may indicate a starting point within the pre-allocated new file for write operations performed by the particular computing node. The various starting points are indicated by the dashed boxes above the merged file 402 in FIG. 4, which indicate respective start and stop points for write operations performed by the various computing nodes associated with the various data bins 106A-106D. The various computing nodes may thus begin writing to the pre-allocated new file to generate the merged file 402 in parallel by beginning their write operations at different portions of the pre-allocated new file (e.g., based on their respective write operation offsets).

Techniques described hereinabove may facilitate rapid analysis of genome sequences to pursue a variety of scientific ends. However, in some instances, techniques described herein may carry a risk that individual reads may be lost or duplicated (e.g., if aligned reads are not properly distributed or bin boundaries are not properly processed).

Merged File Validation

Figure 5:
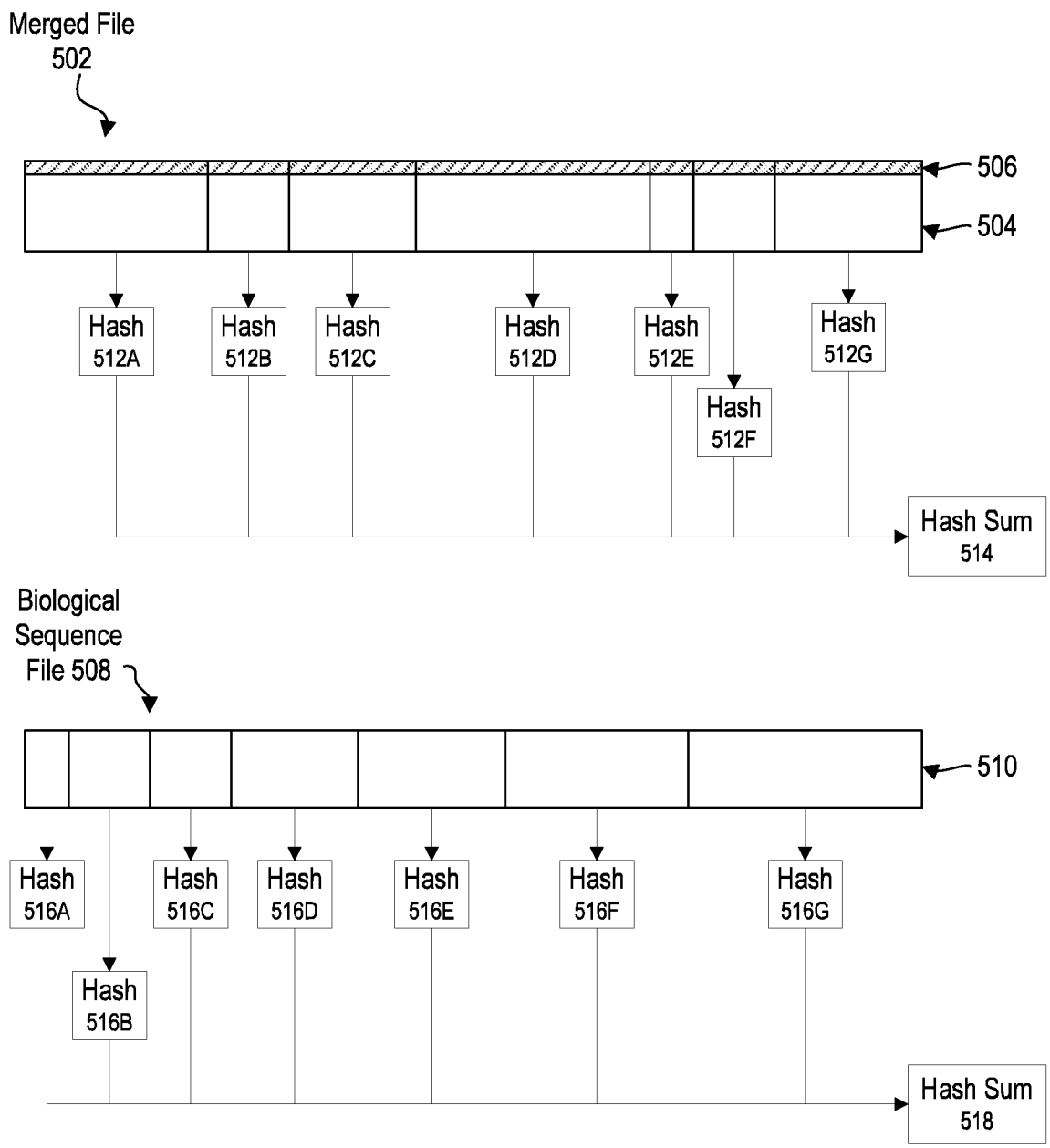
FIGS. 5-7 illustrate conceptual representations of techniques for validating sequence analysis output, in accordance with the present disclosure.
Figure 6:
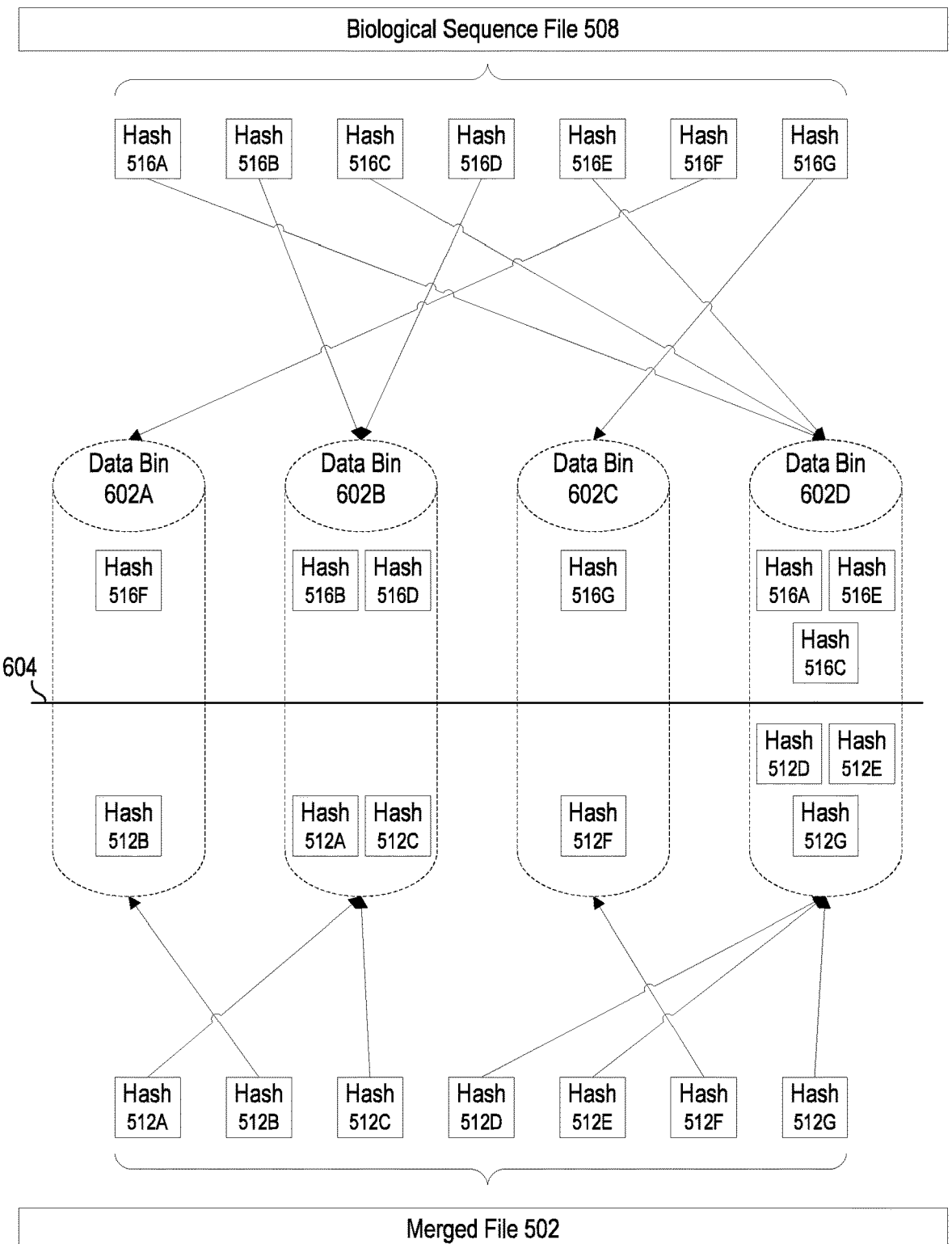
Figure 7:
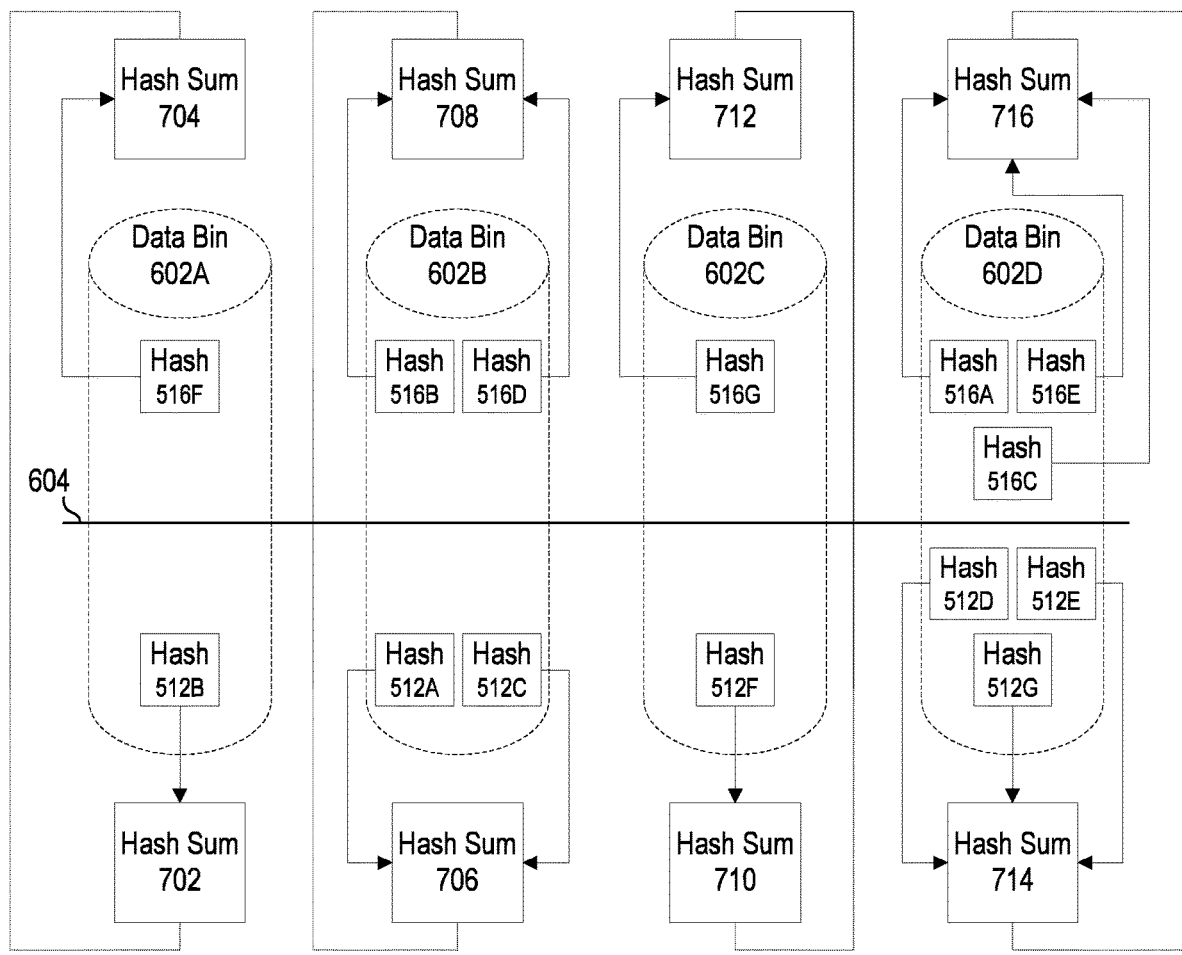

FIGS. 5-7 illustrate conceptual representations of techniques for validating sequence analysis output, in accordance with the present disclosure. In particular, FIG. 5 illustrates a merged file 502 that may correspond, in at least some respects, to the merged file 402 discussed hereinabove with reference to FIG. 4. For example, the merged file 502 as depicted in FIG. 5 includes aligned reads 504 and analysis data 506 associated with the aligned reads. The analysis data may include, for example, alignment information, variant data, and/or other data written to the merged file 502 from a plurality of computing nodes.

FIG. 5 also illustrates a biological sequence file 508 that corresponds, in at least some respects, to the biological sequence file 102 discussed hereinabove with reference to FIGS. 1A and 1B. For example, as shown in FIG. 5, the biological sequence file 508 includes initial reads 510 that were aligned with a reference genome to give rise to the aligned reads 504 of the merged file 502.

To facilitate validation of the merged file 502, a plurality of hashes 512A-512G may be generated from each of the aligned reads 504 of the merged file 502 (e.g., using a fast hash operation). The hashes 512A-512G may be summed to provide a hash sum 514. Similarly, another plurality of hashes 516A-516G may be generated from each of the initial reads 510 of the biological sequence file 508. The hashes 516A-516G may similarly be summed to provide a hash sum 518. Because the merged file 502 and the biological sequence file 508 should contain the same sequence reads (although possibly in a different order, as exaggerated in FIG. 5) the hash sum 514 should substantially match the hash sum 518 to indicate a lack of errors in the merged file 502. In one example, if the hash sum 514 matches the hash sum 518 to a precision provided by 64-bit integers, there is only a one in 9 quintillion chance that data was lost or duplicated throughout the generation of the merged file 502. Such techniques allow for order-independent validation of the aligned reads 504 present in the merged file 502 based on the initial reads 510 of the biological sequence file 508.

Additional or alternative validation techniques may be performed in accordance with the present disclosure. For example, FIG. 6 illustrates the various hashes 516A-516G associated with the biological sequence file 508 discussed above. FIG. 6 also illustrates the various hashes 512A-512G associated with the merged file 502 discussed above. To facilitate granular validation of the merged file 502, the various hashes 512A-512G of the merged file 502 and the various hashes 516A-516G of the biological sequence file may be binned into a plurality of data bins 602A-602D, as conceptually represented in FIG. 6 by the arrows extending from the various hashes 516A-516G and 512A-512G to the various data bins 602A-602D.

The various hashes 516A-516G and 512A-512G may be assigned to the various data bins 602A-602D in various ways. In some instances, the various hashes 516A-516G and 512A-512G are assigned to data bins 602A-602D based on one or more modulus operations. For example, because the various hashes 516A-516G may comprise or be represented as integer values (e.g., 64-bit integer values), a system may perform a modulus operation on the hashes 516A-516G and 512A-512G using any desired value (e.g., 1000) to generate a bin number for each of the hashes 516A-516G and 512A-512G (e.g., a bin number between 0 and 999, using 1000 for the modulus operation according to the present example).

In some implementations, as discussed above, because the aligned reads 504 of the merged file 502 and the initial reads 510 of the biological sequence file 508 are hashed individually, there is a one-to-one correspondence between (i) the number of hashes from the group of hashes 516A-516G become assigned to each of the data bins, and (ii) the number of hashes from the group of hashes 512A-512G that become assigned to each of the data bins. To illustrate, FIG. 6 shows the data bin 602A as including a single hash (i.e., hash 516F) from the group of hashes 516A-516G and a single hash (i.e., hash 512B) from the group of hashes 512A-512G. Similarly, FIG. 6 shows data bin 602B as including hashes 516B and 516D from the group of hashes 516A-516G in addition to hashes 512A and 512C from the group of hashes 512A-512G. FIG. 6 furthermore shows data bin 602C as including hash 516G from the group of hashes 516A-516G and hash 512F from the group of hashes 512A-512G. In addition, FIG. 6 shows data bin 602D as including hashes 516A, 516E, and 516C from the group of hashes 516A-516G, as well as hashes 512D, 512D, and 512G from the group of hashes 512A-512G. For clarity, the hashes from the different groups of hashes 516A-516G and 512A-512G in each of the data bins 602A-602D are divided by the line 604.

In this way, individual hashes 516A-516G from initial reads 510 of the biological sequence file 508 may be correlated with the hashes 512A-512G from the aligned reads 504 of the merged file 502 by association with the same data bin(s). Binning to correlate the hashes 516A-516G with the hashes 512A-512G may facilitate more granular validation of the merged file 502. For instance, FIG. 7 illustrates the various hashes 516A-516G and 512A-512D distributed among the data bins 602A-602D, as discussed above with reference to FIG. 6.

FIG. 7 illustrates that hash sums may be generated for each set of hash sums assigned to a common data bin from the same group of hashes. For example, FIG. 7 shows that hash 516F, which was assigned to data bin 602A from the group of hashes 516A-516G associated with the biological sequence file 508, may be used to generate hash sum 704, and FIG. 7 shows that hash 512B, which was assigned to data bin 602A from the group of hashes 512A-512G associated with the merged file 502, may be used to generate hash sum 702. Furthermore, for data bin 602B, FIG. 7 shows that hashes 516B and 516D may be used to generate hash sum 708, and that hashes 512A and 512C may be used to generate hash sum 706. FIG. 7 also illustrates, for data bin 602C, that hash 516G may be used to generate hash sum 712, and that hash 512F may be used to generate hash sum 710. In addition, FIG. 7 shows, for data bin 602D, that hashes 516A, 516E, and 516C may be used to generate hash sum 716, and that 512D, 5412E, and 512G may be used to generate hash sum 714.

The various sums illustrated in FIG. 7 may be generated as running sums as the various hashes 512A-512G and 516A-516G become assigned to data bins 602A-602D as discussed above. Such techniques may allow the hash sums to advantageously be generated in parallel, in particular because the order of summing is irrelevant.

The hash sums 704, 708, 712, and 716 (generated based on the hashes 516A-516G of the biological sequence file 508 assigned to the various data bins 602A-602D) may be compared with the hash sums 702, 706, 710, and 714 (generated based on the hashes 512A-512G of the merged file 508 assigned to the various data bins 602A-602D) to facilitate granular validation of the merged file 502.

For example, hash sums 702 and 704 (which are both associated with data bin 602A) may be compared, as indicated in FIG. 7 by a dotted line extending between hash sum 702 and hash sum 704. A discrepancy between hash sum 704 and hash sum 702 may indicate that a duplication, omission, or other error exists in the portion of the merged file 502 associated with or attributable to data bin 602A (e.g., the aligned read of the merged file 502 that was used to generate the hash 512B, which was assigned to data bin 602A and used to generate the hash sum 702). Similarly, a discrepancy between hash sums 708 and 706 may indicate the existence of one or more errors in the aligned reads of the merged file 502 used to generate hashes 512A and/or 512C, and a discrepancy between hash sums 710 and 712 may indicate the existence of one or more errors in the aligned reads of the merged file 502 used to generate hash 512F. Furthermore, a discrepancy between hash sums 714 and 716 may indicate the existence of one or more errors in the aligned reads of the merged file 502 used to generate hashes 512D, 512E, and/or 512G.

The technique of binning hashes as discussed by example above may provide the advantageous ability to identify which subset of data is responsible for a mismatch. Linear search or pairwise comparison of data associated with a data bin that gives rise to a difference in hash sums may then be performed (e.g., in parallel fashion) to identify a specific read that is missing or duplicated. Such functionality may allow for the identification of a single problematic read out of billions of reads in hundreds of gigabytes of data in a matter of seconds or minutes.

In some instances, the techniques for binning hashes as discussed above may be performed in response to determining that a difference exists between global hashes (e.g., a difference between hash sums 514 and 518), as discussed hereinabove with reference to FIG. 5.

The quantity of the hashes, aligned reads, analysis data, initial reads, data bins, hashes, hash sums, etc. depicted in FIGS. 5-7 are provided as an example only and are not limiting of the present disclosure.

Exemplary Methods of Rapid Genome Sequence Analysis

The following discussion now refers to a number of methods and method acts that may be performed (e.g., by one or more systems that includes hardware elements discussed herein, such as a compute cluster including a plurality of compute nodes). Although the method acts are discussed in a certain order and illustrated in a flow chart as occurring in a particular order, no particular ordering is required unless specifically stated, or required because an act is dependent on another act being completed prior to the act being performed. One will appreciate that certain embodiments of the present disclosure may omit one or more of the acts described herein.

Figure 8:
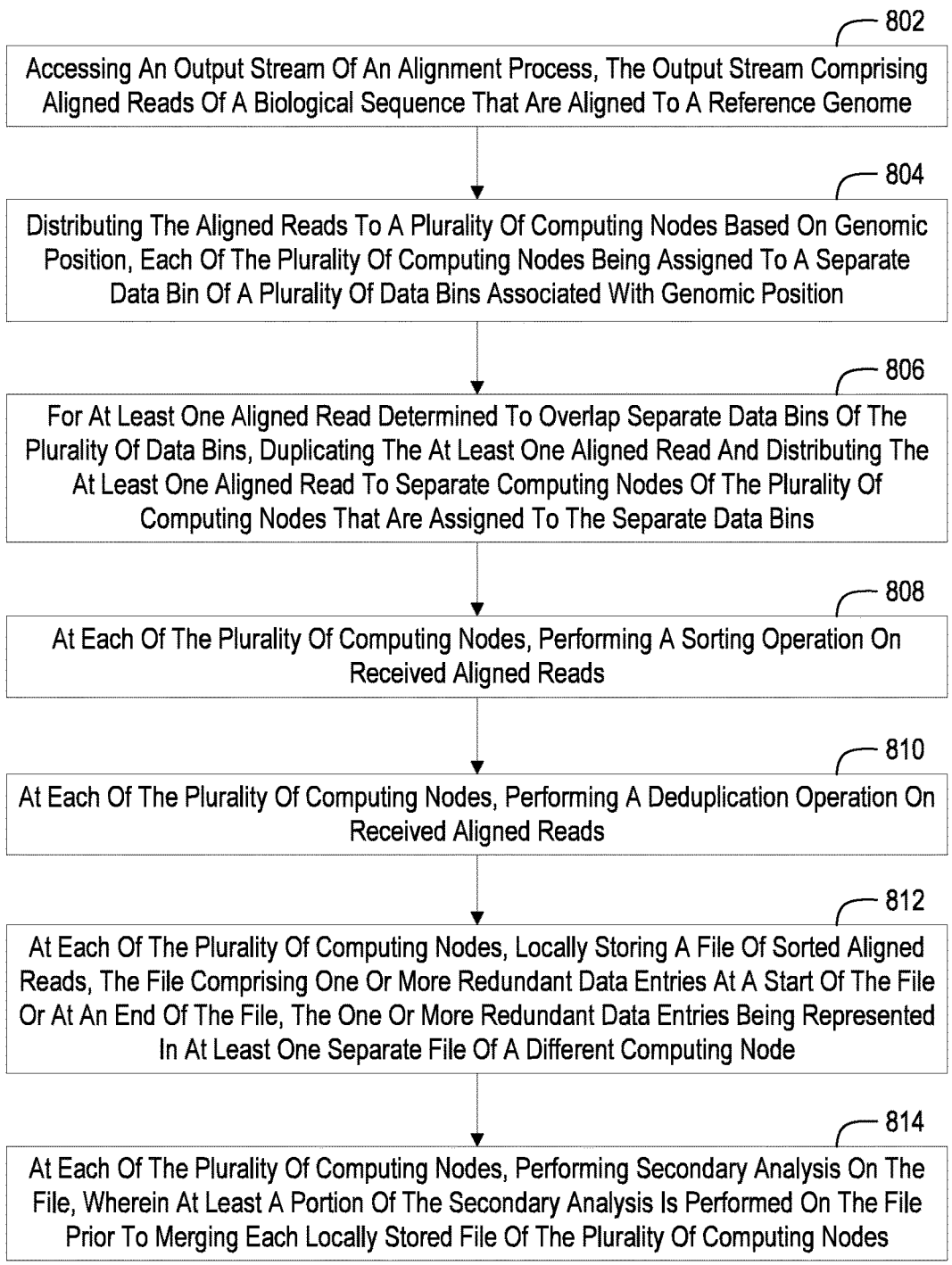
Figure 10:
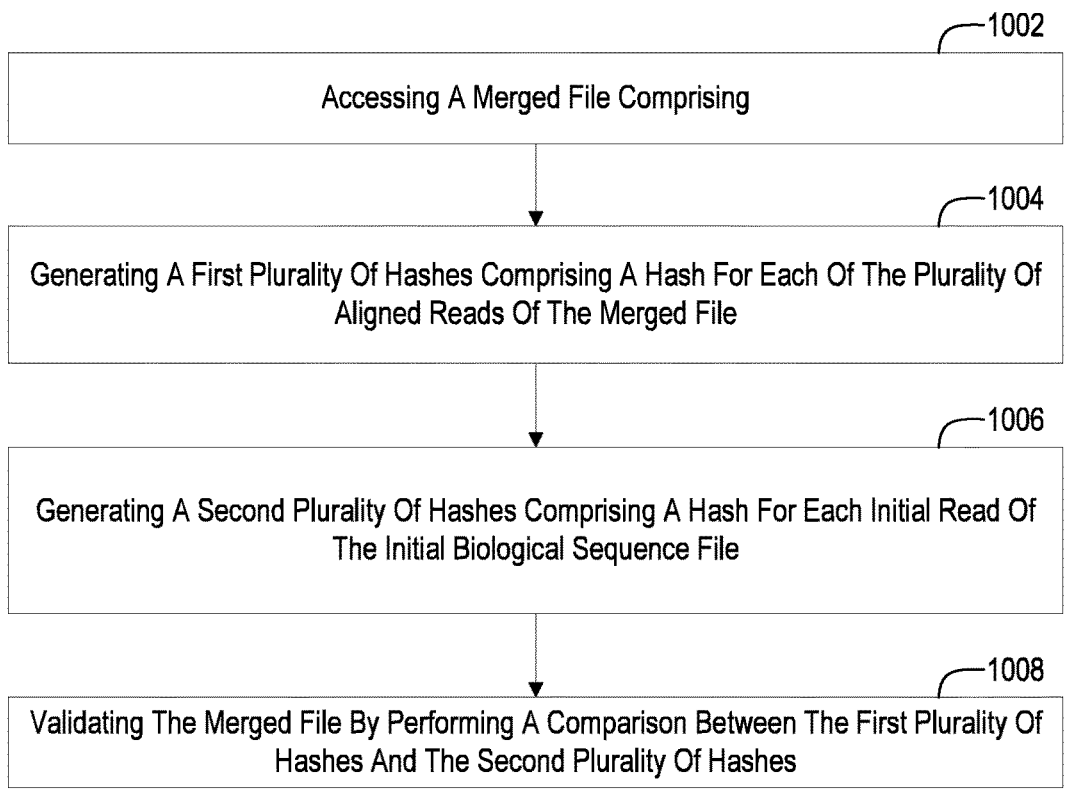

FIGS. 8-10 illustrate example flow diagrams 800, 900, and 1000, respectively, depicting acts associated with facilitating rapid genome sequence analysis. The methods associated with diagrams 800, 900, and 1000 can incorporate and utilize one or more of the system features described above with respect to FIGS. 1-7.

Act 802 of flow diagram 800 includes accessing an output stream of an alignment process, the output stream comprising aligned reads of a biological sequence that are aligned to a reference genome. In some instances, the alignment process comprises a Burrows-Wheeler Aligner (BWA) operating on input data from a FASTQ file.

Act 804 of flow diagram 800 includes distributing the aligned reads to a plurality of computing nodes based on genomic position, each of the plurality of computing nodes being assigned to a separate data bin of a plurality of data bins associated with genomic position. In some instances, a bin size for each data bin of the plurality of data bins comprises a power of 2.

Furthermore, in some instances, distributing the aligned reads to the plurality of computing nodes based on genomic position includes various sub-acts. The sub-acts may include, for each particular aligned read, (i) determining one or more particular data bins of the plurality of data bins by bit shifting one or more genomic positions of the particular aligned read, and (ii) distributing the particular aligned read to each computing node assigned to the one or more particular data bins.

Act 806 of flow diagram 800 includes, for at least one aligned read determined to overlap separate data bins of the plurality of data bins, duplicating the at least one aligned read and distributing the at least one aligned read to separate computing nodes of the plurality of computing nodes that are assigned to the separate data bins.

Act 808 of flow diagram 800 includes, at each of the plurality of computing nodes, performing a sorting operation on received aligned reads (e.g., a Sambamba sort). In some instances, at least a portion of the sorting operation is performed contemporaneously with the distribution of aligned reads to the plurality of computing nodes.

Act 810 of flow diagram 800 includes, at each of the plurality of computing nodes, performing a deduplication operation on received aligned reads (e.g., a Samblaster deduplication). In some implementations, at least a portion of the deduplication operation is performed contemporaneously with the distribution of aligned reads to the plurality of computing nodes.

Act 812 of flow diagram 800 includes, at each of the plurality of computing nodes, locally storing a file of sorted aligned reads, the file comprising one or more redundant data entries at a start of the file or at an end of the file, the one or more redundant data entries being represented in at least one separate file of a different computing node.

Act 814 of flow diagram 800 includes, at each of the plurality of computing nodes, performing secondary analysis on the file, wherein at least a portion of the secondary analysis is performed on the file prior to merging each locally stored file of the plurality of computing nodes. In some instances, the secondary analysis comprises a sequence polishing operation (e.g., GATK IndelRealigner and BaseRecalibrator, Pilon, Racon, etc.). In some instances, the secondary analysis comprises a calling operation (e.g., HaplotypeCaller).

Attention is now directed to FIG. 9, which illustrates flow diagram 900. Act 902 of flow diagram 900 includes accessing a plurality of files, each of the plurality of files being stored locally on a separate computing node of a plurality of computing nodes, each of the plurality of files being generated based on aligned reads of a biological sequence that are aligned to a reference genome, each particular file of the plurality of files comprising non-indexed independent compression blocks, each file of the plurality of files comprising one or more compressed representations of one or more redundant data entries at a start of the file or at an end of the file, the one or more redundant data entries being represented in at least one separate file of the plurality of files. In some instances, the plurality of files corresponds to the files of act 812.

Act 904 of flow diagram 900 includes, for each particular file of the plurality of files, determining a respective region of interest by selectively decompressing fewer than all of the independent compression blocks of the particular file to identify a respective start boundary or a respective end boundary for the particular file, the respective region of interest being bounded by at least the respective start boundary or the respective end boundary, wherein data entries preceding the respective start boundary are represented in at least one separate file of the plurality of files, and wherein data entries following the respective end boundary are represented in at least one separate file of the plurality of files.

In some implementations, for at least one particular file of the plurality of files, determining the respective region of interest includes various sub-acts, which may include (i) determining that the respective start boundary or the respective end boundary resides within a particular compression block, and (ii) splitting the particular compression block and rebuilding separate compression blocks about the respective start boundary or the respective end boundary.

Act 906 of flow diagram 900 includes generating a merged file from the plurality of files by causing each particular computing node of the plurality of computing nodes to write respective data entries from compression blocks within the respective region of interest of the corresponding file to generate the merged file in parallel. In some instances, generating the merged file includes various sub-acts, which may include (i) pre-allocating a new file using an expected size, the expected size being determined based on the respective regions of interest of the plurality of files, (ii) for each particular computing node of the plurality of computing nodes, determining a respective write operation offset based on a binning associated with each of the plurality of files and based on the respective regions of interest of the plurality of files, and (iii) causing each particular computing node of the plurality of computing nodes to write the respective data entries to the new file using its respective write operation offset.

Attention is now directed to FIG. 10, which illustrates flow diagram 1000. Act 1002 of flow diagram 1000 includes accessing a merged file comprising. The merged file includes a plurality of aligned reads of a biological sequence. The plurality of aligned reads are written to the merged file from respective files of a plurality of computing nodes, and the respective files are generated based on binning alignment output that aligns initial reads of an initial biological sequence file to a reference genome. The merged file also includes analysis data for each of the plurality of aligned reads. The analysis data is written to the merged file from the respective files of the plurality of computing nodes, and the analysis data is generated at the plurality of computing nodes for the respective files.

In some instances, the merged file corresponds to the merged file from act 906. Furthermore, in some instances, the analysis data includes one or more differences between the reference genome and the plurality of aligned reads.

Act 1004 of flow diagram 1000 includes generating a first plurality of hashes comprising a hash for each of the plurality of aligned reads of the merged file. Act 1006 of flow diagram 1000 includes generating a second plurality of hashes comprising a hash for each initial read of the initial biological sequence file.

Act 1008 of flow diagram 1000 includes validating the merged file by performing a comparison between the first plurality of hashes and the second plurality of hashes. In some instances, performing the comparison between the first plurality of hashes and the second plurality of hashes includes various sub-acts, which may include (i) calculating a first sum of the first plurality of hashes, (ii) calculating a second sum of the second plurality of hashes, (iii) comparing the first sum to the second sum.

Furthermore, in some instances, the first plurality of hashes is associated with at least one of a plurality of data bins based on one or more modulus operations. In such instances, the sub-acts for performing the comparison between the first plurality of hashes and the second plurality of hashes may include (i) assigning each of the second plurality of hashes to one or more data bins of the plurality of data bins based on one or more modulus operations, and (ii) for each particular data bin of the plurality of data bins, searching for discrepancies between at least a first hash of the first plurality of hashes assigned to the particular data bin and at least a second hash of the second plurality of hashes assigned to the particular data bin.

Additional Computer System Details

A system configured for implementing disclosed techniques may include various hardware elements, such as one or more processors and/or one or more hardware storage devices. A system may comprise any number of additional or alternative components and may take on various forms (e.g., a single computing node of a compute cluster, an entire compute cluster, etc.).

A processor may comprise one or more sets of electronic circuitry that include any number of logic units, registers, and/or control units to facilitate the execution of computer-readable instructions (e.g., instructions that form a computer program). Such computer-readable instructions may be stored within computer-readable storage (e.g., hardware storage). The storage may comprise physical system memory and may be volatile, non-volatile, or some combination thereof. Furthermore, storage may comprise local storage, remote storage (e.g., accessible via communication system(s) or otherwise), or some combination thereof.

Processors may be configured to execute instructions stored within computer-readable storage to perform certain actions associated with facilitating rapid genome sequence analysis. The actions may rely at least in part on data stored on computer-readable storage in a volatile or non-volatile manner.

In some instances, the actions may rely at least in part on one or more communication systems for receiving data and/or instructions from one or more remote systems, which may include, for example, separate systems or computing devices/nodes/clusters, sensors, and/or others. The communications system(s) may comprise any combination of software or hardware components that are operable to facilitate communication between on-system components/devices and/or with off-system components/devices. For example, the communications system(s) may comprise MPI structures, ports, buses, or other connection apparatuses for communicating with other devices/components. Additionally, or alternatively, the communications system(s) may comprise systems/components operable to communicate wirelessly with external systems and/or devices through any suitable communication channel(s), such as, by way of non-limiting example, Bluetooth, ultra-wideband, Wi-Fi, MILAN, infrared communication, and/or others.

Disclosed embodiments may comprise or utilize a special purpose or general-purpose computer including computer hardware, as discussed in greater detail below. Disclosed embodiments also include physical and other computer-readable media for carrying or storing computer-executable instructions and/or data structures. Such computer-readable media can be any available media that can be accessed by a general-purpose or special-purpose computer system. Computer-readable media that store computer-executable instructions in the form of data are one or more "physical computer storage media" or "hardware storage device(s)." Computer-readable media that merely carry computer-executable instructions without storing the computer-executable instructions are "transmission media." Thus, by way of example and not limitation, the current embodiments can comprise at least two distinctly different kinds of computer-readable media: computer storage media and transmission media.

Computer storage media (aka "hardware storage device") are computer-readable hardware storage devices, such as RANI, ROM, EEPROM, CD-ROM, solid state drives ("SSD") that are based on RANI, Flash memory, phase-change memory ("PCM"), or other types of memory, or other optical disk storage, magnetic disk storage or other magnetic storage devices, or any other medium that can be used to store desired program code means in hardware in the form of computer-executable instructions, data, or data structures and that can be accessed by a general-purpose or special-purpose computer.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmissions media can include a network and/or data links which can be used to carry program code in the form of computer-executable instructions or data structures and which can be accessed by a general purpose or special purpose computer. Combinations of the above are also included within the scope of computer-readable media.

Further, upon reaching various computer system components, program code means in the form of computer-executable instructions or data structures can be transferred automatically from transmission computer-readable media to physical computer-readable storage media (or vice versa). For example, computer-executable instructions or data structures received over a network or data link can be buffered in RAM within a network interface module (e.g., a "NIC"), and then eventually transferred to computer system RANI and/or to less volatile computer-readable physical storage media at a computer system. Thus, computer-readable physical storage media can be included in computer system components that also (or even primarily) utilize transmission media.

Computer-executable instructions comprise, for example, instructions and data which cause a general-purpose computer, special purpose computer, or special purpose processing device to perform a certain function or group of functions. The computer-executable instructions may be, for example, binaries, intermediate format instructions such as assembly language, or even source code.

Disclosed embodiments may comprise or utilize cloud computing. A cloud model can be composed of various characteristics (e.g., on-demand self-service, broad network access, resource pooling, rapid elasticity, measured service, etc.), service models (e.g., Software as a Service ("SaaS"), Platform as a Service ("PaaS"), Infrastructure as a Service ("IaaS"), and deployment models (e.g., private cloud, community cloud, public cloud, hybrid cloud, etc.).

Those skilled in the art will appreciate that the invention may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, pagers, routers, switches, wearable devices, and the like. The invention may also be practiced in distributed system environments where multiple computer systems (e.g., local and remote systems), which are linked through a network (either by hardwired data links, wireless data links, or by a combination of hardwired and wireless data links), perform tasks. In a distributed system environment, program modules may be located in local and/or remote memory storage devices.

Alternatively, or in addition, the functionality described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Application-specific Standard Products (ASSPs), System-on-a-chip systems (SOCs), Complex Programmable Logic Devices (CPLDs), central processing units (CPUs), graphics processing units (GPUs), and/or others.

As used herein, the terms "executable module," "executable component," "component," "module," or "engine" can refer to hardware processing units or to software objects, routines, or methods that may be executed on one or more computer systems. The different components, modules, engines, and services described herein may be implemented as objects or processors that execute on one or more computer systems (e.g., as separate threads).

In some implementations, systems of the present disclosure may comprise or be configurable to execute any combination of software and/or hardware components that are operable to facilitate processing using machine learning models or other artificial intelligence-based structures/architectures. For example, one or more processors may comprise and/or utilize hardware components and/or computer-executable instructions operable to carry out function blocks and/or processing layers configured in the form of, by way of non-limiting example, single-layer neural networks, feed forward neural networks, radial basis function networks, deep feed-forward networks, recurrent neural networks, long-short term memory (LSTM) networks, gated recurrent units, autoencoder neural networks, variational autoencoders, denoising autoencoders, sparse autoencoders, Markov chains, Hopfield neural networks, Boltzmann machine networks, restricted Boltzmann machine networks, deep belief networks, deep convolutional networks (or convolutional neural networks), deconvolutional neural networks, deep convolutional inverse graphics networks, generative adversarial networks, liquid state machines, extreme learning machines, echo state networks, deep residual networks, Kohonen networks, support vector machines, neural Turing machines, and/or others.

Various alterations and/or modifications of the inventive features illustrated herein, and additional applications of the principles illustrated herein, which would occur to one skilled in the relevant art and having possession of this disclosure, can be made to the illustrated embodiments without departing from the spirit and scope of the invention as defined by the claims, and are to be considered within the scope of this disclosure. Thus, while various aspects and embodiments have been disclosed herein, other aspects and embodiments are contemplated. While a number of methods and components similar or equivalent to those described herein can be used to practice embodiments of the present disclosure, only certain components and methods are described herein.

It will also be appreciated that systems, devices, products, kits, methods, and/or processes, according to certain embodiments of the present disclosure may include, incorporate, or otherwise comprise properties, features (e.g., components, members, elements, parts, and/or portions) described in other embodiments disclosed and/or described herein. Accordingly, the various features of certain embodiments can be compatible with, combined with, included in, and/or incorporated into other embodiments of the present disclosure. Thus, disclosure of certain features relative to a specific embodiment of the present disclosure should not be construed as limiting application or inclusion of said features to the specific embodiment. Rather, it will be appreciated that other embodiments can also include said features, members, elements, parts, and/or portions without necessarily departing from the scope of the present disclosure.

Moreover, unless a feature is described as requiring another feature in combination therewith, any feature herein may be combined with any other feature of a same or different embodiment disclosed herein. Furthermore, various well-known aspects of illustrative systems, methods, apparatus, and the like are not described herein in particular detail in order to avoid obscuring aspects of the example embodiments. Such aspects are, however, also contemplated herein.

The present disclosure may be embodied in other specific forms without departing from its spirit or essential characteristics. The described embodiments are to be considered in all respects only as illustrative and not restrictive. The scope of the invention is, therefore, indicated by the appended claims rather than by the foregoing description. While certain embodiments and details have been included herein and in the attached disclosure for purposes of illustrating embodiments of the present disclosure, it will be apparent to those skilled in the art that various changes in the methods, products, devices, and apparatus disclosed herein may be made without departing from the scope of the disclosure or of the invention, which is defined in the appended claims. All changes which come within the meaning and range of equivalency of the claims are to be embraced within their scope.

The invention claimed is:

1. A method for facilitating rapid genome sequence analysis, comprising:
   accessing an output stream of an alignment process, the output stream comprising aligned reads of a biological sequence that are aligned to a reference genome;
   distributing the aligned reads to a plurality of data bins based on genomic position, each data bin of the plurality of data bins being assigned to a separate computing node of a plurality of computing nodes associated with genomic position, wherein assigning an aligned read to a data bin corresponds to distributing the aligned read to a corresponding computing node; and
   for at least one aligned read determined to overlap separate data bins of the plurality of data bins, duplicating the at least one aligned read and distributing the at least one aligned read to separate computing nodes of the plurality of computing nodes that are assigned to the separate data bins.

2. The method of claim 1, wherein the alignment process comprises a Burrows-Wheeler Aligner (BWA).

3. The method of claim 1, wherein a bin size for each data bin of the plurality of data bins comprises a power of 2.

4. The method of claim 1, wherein distributing the aligned reads to the plurality of computing nodes based on genomic position comprises, for each particular aligned read:
   determining one or more particular data bins of the plurality of data bins by bit shifting one or more genomic positions of the particular aligned read; and
   distributing the particular aligned read to each computing node assigned to the one or more particular data bins.

5. The method of claim 1, further comprising:
   at each of the plurality of computing nodes, performing a sorting operation on received aligned reads.

6. The method of claim 5, wherein at least a portion of the sorting operation is performed contemporaneously with the distribution of aligned reads to the plurality of computing nodes.

7. The method of claim 1, further comprising, at each of the plurality of computing nodes, performing a deduplication operation on received aligned reads.

8. The method of claim 7, wherein at least a portion of the deduplication operation is performed contemporaneously with the distribution of aligned reads to the plurality of computing nodes.

9. The method of claim 5, further comprising, at each of the plurality of computing nodes, locally storing a file of sorted aligned reads, the file comprising one or more redundant data entries at a start of the file or at an end of the file, the one or more redundant data entries being represented in at least one separate file of a different computing node.

10. The method of claim 9, further comprising, at each of the plurality of computing nodes, performing secondary analysis on the file, wherein at least a portion of the secondary analysis is performed on the file prior to merging each locally stored file of the plurality of computing nodes.

11. The method of claim 10, wherein the secondary analysis comprises a sequence polishing operation.

12. The method of claim 10, wherein the secondary analysis comprises a calling operation.

* * * * *